United States Patent [19]

Dozzi et al.

[11] 4,313,891
[45] Feb. 2, 1982

[54] PROCESS FOR SYNTHESIZING MIXED ALKOXY HYDRIDE DERIVATIVES OF ALUMINIUM AND ALKALINE EARTH METALS

[75] Inventors: Giovanni Dozzi, Milan; Salvatore Cucinella, San Donato Milanese, both of Italy

[73] Assignee: Anic S.p.A., Palermo, Italy

[21] Appl. No.: 88,581

[22] Filed: Oct. 26, 1979

[30] Foreign Application Priority Data

Nov. 10, 1978 [IT] Italy .................................. 29699 A 78
Apr. 4, 1979 [IT] Italy .................................. 21564 A79

[51] Int. Cl.$^3$ .................................................. C07F 5/06
[52] U.S. Cl. .................................. 260/448 AD; 568/8; 568/17; 568/69; 568/846; 568/864; 568/880; 568/881; 568/885; 568/891
[58] Field of Search ................................. 260/448 AD

[56] References Cited

U.S. PATENT DOCUMENTS

| | | | |
|---|---|---|---|
| 2,720,506 | 10/1955 | Caldwell | 260/448 AD X |
| 3,060,216 | 10/1962 | Hamprecht et al. | 260/448 AD |
| 3,147,272 | 9/1964 | Brown et al. | 260/448 AD X |
| 3,184,492 | 5/1965 | Cole | 260/448 AD |
| 3,281,443 | 10/1966 | Hunt | 260/448 AD |
| 3,361,782 | 1/1968 | Ziegler et al. | 260/448 AD |
| 3,394,158 | 7/1968 | Chini et al. | 260/448 AD |
| 3,761,500 | 9/1973 | Thomas | 260/448 AD |
| 3,773,816 | 11/1973 | Honigschmid-Grossich et al. | 260/448 AD |
| 4,120,883 | 10/1978 | Sakurai et al. | 260/448 AD |
| 4,219,491 | 8/1980 | Cucinella | 260/448 AD |

Primary Examiner—Helen M. S. Sneed
Attorney, Agent, or Firm—Morgan, Finnegan, Pine, Foley & Lee

[57] ABSTRACT

This invention relates to a process for synthesizing compounds of aluminium and alkaline earth metals containing hydride hydrogens and alkoxy radicals, of composition $$M[AlH_{4-n}(OR)_n]_2 \cdot xB$$

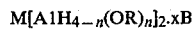

in which $0.5 \leq n \leq 3.5$; OR is an alkoxy radical derived from a primary, secondary or tertiary alcohol; R is an aliphatic, cycloaliphatic or aromatic hydrocarbon radical; M is an alkaline earth metal; B is a Lewis base; x can vary between 0 and 4; and R can also contain functional groups OR', SR', NR'$_2$ ect., consisting of reacting together:
(a) a halide of an alkaline earth metal;
(b) an alanate of an alkaline earth metal of formula M' AlH$_4$ (M'≈alkaline metal);
(c) an alcohol chosen from primary, secondary or tertiary aliphatic, cycloaliphatic or aromatic alcohols containing 1 to 20 carbon atoms.

7 Claims, No Drawings

PROCESS FOR SYNTHESIZING MIXED ALKOXY HYDRIDE DERIVATIVES OF ALUMINIUM AND ALKALINE EARTH METALS

This invention relates to a method for synthesising compounds of aluminium and alkaline earth metals containing hydride hydrogens and alkoxy radicals of composition $$M[AlH_{4-n}(OR)_n]_2 \cdot xB \quad (I)$$

in which $0.5 \leq n \leq 3.5$; OR is an alkoxy radical derived from a primary, secondary or tertiary alcohol; R is an aliphatic, cycloaliphatic or aromatic hydrocarbon radical; M is an alkaline earth metal; B is a Lewis base (cyclic or non-cyclic ethers; trialkylamines); x can vary between 0 and 4; R can also contain functional groups OR', SR', NR'$_2$ etc.

The synthesis method consists of the reaction 1 between an alanate of an alkaline metal, a halide of an alkaline earth metal and an alcohol $$2\,M'AlH_4 + MX_2 + 2nROH \xrightarrow{B} \frac{M\,AlH_{4-n}(OR)_n\,2 \cdot xB}{2\,nM'X + 2n\,H_2} \quad (1)$$

It is known that the alkaline metal alanates, i.e. the starting compounds for reaction 1, can be prepared both by direct synthesis from its elements, and by reacting an aluminium halide with an alkaline metal hydride, and in particular by reacting AlCl$_3$ with a hydride of an alkaline metal in ethyl ether (reaction 2).

$$4\,M'H + AlCl_3 \xrightarrow{Et_2O} M'AlH_4 + 3\,M'Cl \quad (2)$$

In this latter case, by using for example NaH, sodium chloride precipitates together with NaAlH$_4$ from the reaction mixture.

The discovered process enables the synthesis of I to be carried out by using an NaAlH$_4$—NaCl mixture, the constituents of which are in the molar ratio 1:3, as deriving from reaction 2. The extraction of NaAlH$_4$ in the pure state can therefore be avoided. NaCl does not interfere with reaction 1, and in all cases the final product I is obtained at high yield, with a high degree of purity, and at a good reaction rate.

The reaction proceeds in organic solvents of the ether and/or hydrocarbon type. The presence of a Lewis base is preferable, as this has an accelerating effect on the reaction, and at the end of the reaction this base can form a complex with the alkoxy alanate of the alkaline earth metal. The Lewis base can constitute the reaction solvent or be present in a quantity close to the quantity required for the formation of the complex.

The reaction temperature can lie between $-40°$ C. and the decomposition temperature of the product. A temperature between $+20°$ C. and the boiling point of the reaction mixture is preferable. It is also preferable to use an excess of MX$_2$.

At the end of the reaction, the product solution is separated from the metal halides by filtration, and the product is recovered preferably by evaporating the solvent, or by crystallisation, by precipitation with a non-solvent or by other methods.

It has been found that the alkoxy alanates of the alkaline earth metals have a good hydrogenating activity towards a large number of organic functions. Generally, the hydrogenation proceeds in a short time under mild temperature conditions. The hydrogenation product is obtained with a high yield, and is free from undesirable by-products. The hydrogenation reaction requires contact between the reducing agent and substrate in an organic solvent which is inert to the hydride hydrogen. For safety reasons, the aromatic hydrocarbons are preferred. Generally, the reaction proceeds towards the formation of soluble intermediates deriving from addition and/or exchange reactions between the reducing agent and the substrate. The hydrogenated products are finally obtained by the hydrolythic decomposition of the intermediates, and, if they are not already present quantitatively in the organic phase, these products can be recovered completely by repeated extraction with a solvent and then purified by known methods.

The correct choice of the OR group for the alkoxy alanate of the alkaline earth metal facilitates the purification of the hydrogenation product from the corresponding ROH, which also results from the hydrolysis reaction.

Some examples of hydrogenation include the hydrogenation of aldehydes, ketones, acids, esters, anhydrides and acid chlorides to alcohols, lactones to diols, and alkyl halides to alkanes in accordance with reactions 3–9, and also the hydrogenation of amides, nitriles and nitro-derivatives to amines, sulphoxides to sulphides, phosphinoxides to phosphines etc., using M[AlH$_2$(OR)$_2$]$_2$:

$$M[AlH_2(OR)_2]_2 + 4R'R''CO \longrightarrow \quad (3)$$
$$\text{INTERMEDIATE} \xrightarrow{+H_2O}$$
$$4R'R''CHOH + 4ROH + 2Al(OH)_3 + M(OH)_2$$

where R'' is hydrogen or alkyl $$3M[AlH_2(OR)_2]_2 + 4R'COOH \longrightarrow \quad (4)$$
$$\text{INTERMEDIATE} \xrightarrow{+H_2O}$$
$$4R'CH_2OH + 12ROH + 4H_2 + 6Al(OH)_3 + 3M(OH)_2$$

$$M[AlH_2(OR)_2]_2 + 2R'COOR'' \longrightarrow \quad (5)$$
$$\text{INTERMEDIATE} \xrightarrow{+H_2O}$$
$$2R'CH_2OH + 2R''OH + 4\,ROH + 2Al(OH)_3 + M(OH)_2$$

$$M[AlH_2(OR)_2]_2 + (R'CO)_2O \longrightarrow \quad (6)$$
$$\text{INTERMEDIATE} \xrightarrow{+H_2O}$$
$$2R'CH_2OH + 4ROH + 2\,Al(OH)_3 + M(OH)_2$$

$$3M[AlH_2(OR)_2]_2 + 6R'COCl \longrightarrow \quad (7)$$
$$\text{INTERMEDIATE} \xrightarrow{+H_2O}$$
$$6R'CH_2OH + 12ROH + 2AlCl_3 + 4Al(OH)_3 + 3M(OH)_2$$

$$M[AlH_2(OR)_2]_2 + 2R'{-}\underset{\underset{O}{|}}{C}{-}O \longrightarrow \quad (8)$$
$$\text{INTERMEDIATE} \xrightarrow{+H_2O}$$
$$2\,HO{-}R'{-}CH_2OH + 4\,ROH + 2Al(OH)_3 + M(OH)_2$$

$$M[AlH_2(OR)_2]_2 + 4RX \longrightarrow M[AlX_2(OR)_2]_2 + 4RH \quad (9)$$

where X is a halogen.

In addition to use as general hydrogenation agents, the alkoxyalanates of the alkaline earth metals can be used for selective hydrogenation. For example, type I derivatives from alcohols with radicals of large steric bulk and/or with a high value of n can be used for stereo and regioselective hydrogenation. Type I derivatives from alcohols with radicals containing centres of asymmetry can be used in the hydrogenation of prochiral substrates or in the selective reduction of a mixture of enantiomers to give in both cases products with optical activity etc. Selective hydrogenation reactions between different organic functions can also be obtained by using the alkoxyalanates of the alkaline earth metals at low temperature, preferably less than 0° C., as these make the various organic functions subject to different levels of attack by the reducing agent.

The compounds according to the present invention can also be used as drying agents for solvents.

Said compounds can be prepared by reacting an alkaline metal alanate and a halide of an alkaline earth metal with an aldehyde or ketone, in accordance with the general reactions 1 or 2.

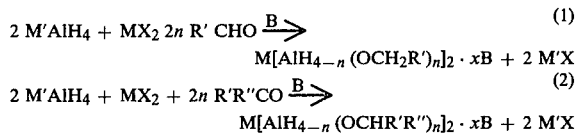

in which R' and R" can be the same or different.

For both the reactions, the symbols M, B, n and x have the meaning given for formula I. In addition $CH_2R'$ and $CHR'R''$ are equivalent to R in formula I, M' is an alkaline metal and X is a halogen.

EXAMPLE 1

Preparation of $Ca(AlH_2[OCH(CH_3)_2])_2.2THF$

Operating under a nitrogen atmosphere, 100 ml of a suspension in ether-hexane of $NaAlH_4$ (65.5 mmoles) and NaCl in a molar ratio of 1:3, deriving directly from the preparation of $NaAlH_4$ from NaH and $AlCl_3$ in accordance with the reaction $4NaH + AlCl_3 \rightarrow NaAlH_4 + 3NaCl$, are placed in a 500 ml flask provided with a filling funnel and a bulb condenser.

It is allowed to decant for 2 hours, and the overlying liquid phase (40 ml) is removed by syphoning, and is replaced by the same quantity of THF.

7.8 g of powdered $CaCl_2$ (purity 92%, 65 mmoles) are added, the stirred suspension is heated to the solvent reflux temperature, and a solution containing 10 ml of isopropyl alcohol (131 mmoles) in 30 ml of THF is then added slowly through the filling funnel.

It is left under reflux and stirring until the atomic Ca/Al ratio in solution is close to 0.5 (about 4 hours). The suspension is finally filtered, the residue is washed on the filter three times with 10 ml of THF, and the filtrate, consisting of the mother solution and the wash solutions, is evaporated under reduced pressure to give a solid white product which is weighed (12.7 g) and analysed:

Found Al=11.9%; Ca=8.4%; Hatt=9.2 meq/g corresponding to Ca/Al=0.48; Hatt/Al=2.08.

Theoretical for $C_{20}H_{48}Al_2CaO_6$: Al=11.3%; Ca=8.4%; Hatt=8.4 meq/g; Yield 85%.

EXAMPLE 2

Preparation of $Ca(AlH_2[OC(CH_3)_3])_2.2THF$

The operation is carried out in the same manner and using the same quantities of reagents as in example 1, with the exception that the alcohol used is in this case tertbutyl alcohol (12.35 ml, 131 mmoles). A white solid product is finally obtained, which is weighed (15.3 g) and analysed:

Found Al=10.2%; Ca=7.2%; Hatt=8.0 meq/g corresponding to Ca/Al=0.48; Hatt/Al=2.1.

Theoretical for $C_{24}H_{56}Al_2CaO_6$: Al=10.1%; Ca=7.5%; Hatt=7.5 meq/g; Yield 88%.

EXAMPLE 3

Preparation of $Ca(AlH_2[OCH_2CH(CH_3)_2]_2)_2.THF$

Operating under a nitrogen atmosphere, 100 ml of a suspension in ether-hexane of $NaAlH_4$ (65 mmoles) and NaCl in a molar ratio of 1:3 deriving directly from the preparation of $NaAlH_4$ (see example 1) are placed in a 250 ml flask.

The solvent is evaporated completely under reduced pressure and then 9.5 g of powdered $CaCl_2$ (purity 92%, 79 mmoles), 20 ml of THF and 80 ml of toluene are added in that order.

The suspension is stirred, heated to reflux temperature, and a solution containing 12 ml of isobutanol (130 mmoles) in 40 ml of toluene is then added slowly.

It is left at reflux temperature under stirring for 8 hours.

The suspension is filtered, the residue is washed on the filter with toluene, and the filtrate consisting of the mother solution and the wash solution is evaporated under reduced pressure to give a white solid product which is weighed (12.3 g) and analysed:

Found Al=12.8%; Ca=9.6%; Hatt=9.2 meq/g corresponding to Ca/Al=0.50; Hatt/Al=1.94.

Theoretical for $C_{20}H_{48}Al_2CaO_5$: Al=11.7%; Ca=8.7%; Hatt=8.7 meq/g. Yield 89%.

EXAMPLE 4

Preparation of $Ca(AlH_2[OCH_2CH(CH_3)_2]_2)_2$

Operating under a nitrogen atmosphere, 100 ml of a suspension in ether-hexane of $NaAlH_4$ (70 mmoles) and NaCl in a molar ratio of 1:3 deriving directly from the preparation of $NaAlH_4$ (see example 1) are placed in a 250 ml flask provided with a filling funnel and a bulb condenser. It is allowed to decant, the overlying liquid phase (40 ml) is removed, and is replaced by 130 ml of diethyl ether and 10 ml of THF.

After adding 17 g of powdered $CaCl_2$ (purity 92%, 140 mmoles), the suspension is heated to the reflux temperature of the solvent, and a solution containing 12.9 ml of isobutanol (140 mmoles) in 40 ml of ether is then added slowly.

After this addition, the mixture is left under stirring at the reflux temperature until a Ca/Al ratio of 0.5 is obtained in the solution (about 5 hours).

It is filtered, the residue is washed on the filter with ether, and the filtrate consisting of the mother solution and the wash solution is evaporated under reduced pressure to give a white solid product which is weighed (13.3 g) and analysed:

Found Al=13.4%; Ca=9.9%; Hatt=9.5 meq/g corresponding to Ca/Al=0.5; Hatt/Al=1.91.

Theoretical for $C_{16}H_{40}Al_2CaO_4$: Al=13.8%; Ca=10.3%; Hatt=10.2 meq/g; Yield 94%.

EXAMPLE 5

Preparation of $Ca(AlH_2[OCH_2CH(CH_3)_2]_2)_2.2THF$

Operating under a nitrogen atmosphere, 28 g of a solid product containing $NaAlH_4$ (120 mmoles) and NaCl in a molar ratio of 1:3 obtained as in example 3 are transferred into a 500 ml flask provided with a filling funnel and a bulb condenser. 24 g of powdered $CaCl_2$ (purity 92%, 200 mmoles) and then 20 ml of THF and 130 ml of methyl-tert-butyl ether are then added.

The suspension thus obtained is stirred and heated to the solvent reflux temperature, and a solution containing 22.2 ml of isobutanol (240 mmoles) in 50 ml of methyl-tert-butyl ether is then slowly added.

After this addition, it is left under stirring at the reflux temperature until a Ca/Al ratio of 0.5 is obtained in the solution (about 40 minutes).

It is filtered, and the filtrate is evaporated under reduced pressure to give a white solid product which is weighed (23 g) and analysed:

Found Al=9.9%; Ca=7.5%; Hatt=7.1 meq/g corresponding to Ca/Al=0.51; Hatt/Al=1.93.

Theoretical for $C_{24}H_{56}Al_2CaO_6$: Al=10.1%; Ca=7.5%; Hatt=7.5 meq/g; Yield 70%.

EXAMPLE 6

Preparation of $Ca(AlH_{2.5}[OCH_2CH(CH_3)_2]_{1.5})_2.THF$

Operating in a nitrogen atmosphere, 70 ml of a suspension in ether-hexane of $NaAlH_4$ (45.5 mmoles) and NaCl in a molar ratio of 1:3 deriving directly from the preparation of $NaAlH_4$ (see example 1) are placed in a 250 ml flask provided with a filling funnel and a bulb condenser.

It is allowed to decant, the overlying liquid phase (30 ml) is removed, and is replaced by 40 ml of THF.

After adding 6.5 g of powdered $CaCl_2$ (purity 92%), 54 mmoles), the stirred suspension is heated to the solvent reflux temperature, and a solution containing 6.3 ml of isobutanol (68.2 mmoles) in 40 ml of toluene is slowly added.

After this addition, it is left under stirring at reflux temperature until a Ca/Al ratio of 0.5 is obtained in the solution (about 6 hours).

It is filtered, the residue is washed on the filter with toluene, and the filtrate consisting of the mother solution and the wash solution is evaporated under reduced pressure to give a white solid product which is weighed (7.35 g) and analysed:

Found Al=14.7%; Ca=11.0%; Hatt=13.5 meq/g corresponding to Ca/Al=0.5; Hatt/Al=2.5.

Theoretical for $C_{16}H_{40}Al_2CaO_4$: Al=13.8%; Ca=10.3%; Hatt=12.8 meq/g; Yield 88%.

EXAMPLE 7

Preparation of $Ca(AlH_2[OCH_2CH(CH_3)_2]_2)_2.THF$

Operating under a nitrogen atmosphere, 3.5 g of pure $NaAlH_4$ (65 mmoles) dissolved in 130 ml of THF are placed in a 500 ml flask provided with a filling funnel and a bulb condenser.

Approximately 9 g of powdered $CaCl_2$ (purity about 92%, 75 mmoles) are added, and the stirred suspension is heated to the solvent reflux temperature.

A solution containing 12 ml of isobutanol (130 mmoles) in 40 ml of THF is slowly added through the filling funnel.

It is then left stirring under reflux for 1 hour.

The suspension is filtered, the residue is washed on the filter with THF, and the filtrate consisting of the mother solution and the wash solution is evaporated under reduced pressure to give a white solid product which is weighed (14.8 g) and analysed:

Found Al=11.3%; Ca=8.2%; Hatt=8.0 meq/g corresponding to Ca/Al=0.49%; Hatt/Al=1.9.

Theoretical for $C_{20}H_{48}Al_2CaO_5$: Al=11.7%; Ca=8.7%; Hatt=8.7 meq/g; Yield 95%.

EXAMPLE 8

Preparation of $Ca(AlH_2[OCH_2CH_2CH(CH_3)_2]_2)_2$

Operating under a nitrogen atmosphere, 100 ml of a suspension in ether-hexane of $NaAlH_4$ (78 mmoles) and NaCl in a molar ratio of 1:3 deriving directly from the preparation of $NaAlH_4$ (see example 1) are placed in a 500 ml flask provided with a filling funnel and a bulb condenser.

It is allowed to decant for 2 hours, and the overlying liquid phase (40 ml) is removed by syphoning, and is replaced by the same quantity of THF.

9 g of powdered $CaCl_2$ (purity 92%, 75 mmoles) are then added, the stirred suspension is heated to the solvent reflux temperature, and a solution containing 17 ml of isoamyl alcohol (156 mmoles) in 40 ml of THF is then added slowly through the filling funnel.

It is left stirring under reflux for about 3 hours.

The suspension is finally filtered, the residue is washed on the filter three times with 15 ml of THF, and the wash solutions are combined with the mother solution. The resultant solution is evaporated under reduced pressure to give a white solid product which is weighed (17 g) and analysed;

Found Al=11.2%; Ca=8.1%; Hatt=8.08 meq/g corresponding to Ca/Al=0.49; Hatt/Al=1.95.

Theoretical for $C_{20}H_{48}Al_2CaO_4$: Al=12.1%; Ca=9.0%; Hatt=9.0 meq/g; Yield 91%.

EXAMPLE 9

Preparation of $Ca[AlH_2(OCH_2CH_2OCH_3)_2]_2$

Operating under a nitrogen atmosphere, 140 ml of a suspension in ether-hexane of $NaAlH_4$ (91 mmoles) and NaCl in a molar ratio of 1:3 deriving directly from the preparation of $NaAlH_4$ (see example 1) are placed in a 2 neck 500 ml flask.

7.5 g of powdered $CaCl_2$ (purity 92%, 62 mmoles) are added, and the ether-hexane solvent is completely removed by evaporation under reduced pressure. 140 ml of toluene are added to the residue consisting of $NaAlH_4$ and NaCl.

A bulb condenser and a filling funnel are mounted on the flask.

The suspension is stirred with a magnetic stirrer and is heated to the solvent reflux temperature.

A solution containing 14.2 ml of 2-methoxyethanol (180 mmoles) in 45 ml of toluene is then slowly added through the filling funnel.

It is left stirring at reflux temperature for about 6 hours.

It is then filtered, the residue is washed three times on the filter with 15 ml of toluene, and the filtrate consisting of the mother solution and the wash solutions is evaporated under reduced pressure to give a white solid product which is weighed (15.4 g) and analysed:

Found Al=12.3%; Ca=9.1%; Hatt=8.7 meq/g corresponding to Ca/Al=0.5; Hatt/Al=1.9.

Theoretical for $C_{12}H_{32}Al_2CaO_8$: Al=13.5%; Ca=10.1%; Hatt=10.1 meq/g; Yield 77%.

EXAMPLE 10

Preparation of $Ca[AlH_2(OCH_2CH_2OCH_3)_2]_2$

Operating in the same manner as example 6, with the exception that in this case the solvent is diethyl ether and the quantity of CaCl$_2$ is 30 g, a final white solid product is obtained which is dried, weighed (12 g) and analysed:

Found Al=12.6%; Ca=9.1%; Hatt=9.5 meq/g corresponding to Ca/Al=0.49; Hatt/Al=2.04.

Theoretical for C$_{12}$H$_{32}$Al$_2$CaO$_8$: Al=13.5%; Ca=10.1%; Hatt=10.1 meq/g; Yield approximately 60%.

EXAMPLE 11

Preparation of Ca[AlH$_2$(OCH$_2$CH$_2$OCH$_3$)$_2$]$_2$

Operating under a nitrogen atmosphere, 150 ml of a solution containing LiAlH$_4$ (80 mmoles) in diethyl ether is placed in a 500 ml flask provided with a filling funnel and a bulb condenser.

24 g of powdered CaCl$_2$ (purity 92%, 200 mmoles) are then added. The stirred suspension is heated to the solvent reflux temperature, and a solution containing 12.6 ml of 2-methoxyethanol (160 mmoles) in 50 ml of ether is then added slowly through the filling funnel.

It is left stirring under reflux for about 4 hours, and the Ca/Al and Hatt/Al ratios in the solution are then checked, these being:

Ca/Al=0.48 Hatt/Al=1.85

EXAMPLE 12

Operating under a nitrogen atmosphere, 1 ml of a toluene solution containing 1 mmole of n-butyric aldehyde is added at ambient temperature to 1.5 ml of a stirred toluene solution containing 0.375 mmoles of Ca[AlH$_2$(OCH$_2$CH$_2$OCH$_3$)$_2$]$_2$.

There is an immediate exothermic reaction. It is then kept stirred for 15 minutes at ambient temperature. It is cooled and hydrolysed with an aqueous 6 N solution of H$_2$SO$_4$.

After decanting, the organic phase is recovered, dried through molecular sieve and analysed by gas chromatography.

The yield of n-butanol deriving from the reduction of the butyric aldehyde is quantitative.

EXAMPLE 13

Operating in accordance with the method of example 1, 1 ml of a toluene solution containing 1 mmole of benzaldehyde is added at ambient temperature to 1.5 ml of a stirred toluene solution containing 0.375 mmoles of Ca(AlH$_2$[OCH$_2$CH(CH$_3$)$_2$]$_2$)$_2$2THF. It is kept under stirring for 1 hour at ambient temperature. After acid hydrolysis, the toluene solution is analysed by gas chromatography. The yield of benzyl alcohol deriving from the reduction of the benzaldehyde is quantitative.

EXAMPLE 14

Operating in accordance with the method of example 1, 1 mmole of 4-methyl-2-pentanone in 1 ml of toluene is reacted with 0.375 mmoles of Ca[AlH$_2$(OCH$_2$CH$_2$OCH$_3$)$_2$]$_2$ dissolved in 1.5 ml of toluene. It is kept under stirring for 30 minutes at ambient temperature. After acid hydrolysis, the resultant toluene solution is analysed by gas chromatography. The yield of 4-methyl-2-pentanol deriving from the reduction of the 4-methyl-2-pentanone is 99.5%.

EXAMPLE 15

Operating in accordance with the method of example 1, 1 ml of a toluene solution containing 1 mmole of cyclohexanone is reacted with 0.375 mmoles of Ca[AlH$_2$(Otert.C$_4$H$_9$)$_2$]$_2$.2THF dissolved in 1.5 ml of toluene. It is kept under stirring for 1 h at ambient temperature. After acid hydrolysis, the resultant toluene solution is analysed by gas chromatography. The yield of cyclohexanol deriving from the reduction of the cyclohexanone is quantitative.

EXAMPLE 16

Operating in accordance with the method of example 1, 1 mmole of caproic acid in toluene (1 ml of a 1 M solution) is reacted with 1 mmole of Ca[AlH$_2$(OisoC$_4$H$_9$)$_2$]$_2$.THF in toluene (3.2 ml of a 0.313 M solution) for 3.5 hours at 80° C.

After acid hydrolysis, the resultant toluene solution is analysed by gas chromatography.

The yield of n-hexanol deriving from the reduction of the caproic acid is quantitative.

EXAMPLE 17

Operating in accordance with the method of example 1, 1 mmole of ethyl caproate in toluene (1 ml of a 1 M solution) is reacted with 0.75 mmoles of Ca[AlH$_2$(Otert.C$_4$H$_9$)$_2$]$_2$.2THF in toluene (2.5 ml of a 0.3 M solution) for 30 minutes at ambient temperature. After acid hydrolysis, the resultant toluene solution is analysed by gas chromatography. The yield of n-hexanol deriving from the reduction of the ethyl caproate is quantitative.

EXAMPLE 18

Operating in accordance with the method of example 1, 1 mmole of ethyl caproate in toluene (1 ml of a 1 M solution) is reacted with 0.75 mmoles of Ca[AlH$_2$(OisoC$_4$H$_9$)$_2$]$_2$.THF in toluene (2.5 ml of a 0.3 M solution) for 15 minutes at ambient temperature. After acid hydrolysis, the resultant toluene solution is analysed by gas chromatography. The yield of n-hexanol deriving from the reduction of ethyl caproate is quantitative.

EXAMPLE 19

Operating in accordance with the method of example 1, 2 mmoles of ethyl benzoate in toluene (2 ml of a 1 M solution) are reacted with 1.1 mmoles of Ca[AlH$_2$(OisoC$_4$H$_9$)$_2$]$_2$.THF in toluene (3.5 ml of a 0.315 M solution) for 15 minutes at 50° C. After acid hydrolysis, the resultant toluene solution is analysed by gas chromatography. The yield of benzyl alcohol deriving from the reduction of the ethyl benzoate is quantitative.

EXAMPLE 20

Operating under a nitrogen atmosphere, 1 mmole of 4-butyrolactone in toluene (1 ml of a 1 M solution) is reacted with 0.75 mmoles of Ca[AlH$_2$(Otert.C$_4$H$_9$)$_2$]$_2$.2THF in toluene (3.1 ml of a 0.242 M solution). It is kept under stirring for 1 hour at ambient temperature. It is decomposed with a few drops of water and a few ml of methanol are added.

The solution is dried through molecular sieve and analysed by gas chromatography. The yield of 1,4-butanediol deriving from the reduction of the 4-butyrolactone is quantitative.

EXAMPLE 21

Operating by the method of example 1, 1 mmole of benzoyl chloride in toluene (1 ml of a 1 M solution) is reacted with 0.75 mmoles of Ca[AlH$_2$(Otert.C$_4$H$_9$)$_2$]$_2$.2THF in toluene (3 ml of a 0.25 M solution) for 1 hour at ambient temperature. After acid hydrolysis, the resultant toluene solution is analysed by gas chromatography. The yield of benzyl alcohol deriving from the reduction of the benzoyl chloride is 95%.

EXAMPLE 22

Operating by the method of example 1, 1 mmole of benzoyl chloride in toluene (1 ml of a 1 M solution) is reacted with 0.55 mmoles of $Ca[AlH_2(OisoC_4H_9)_2]_2.THF$ in toluene (2.2 ml of a 0.25 M solution) for 1 hour at ambient temperature. After acid hydrolysis, the resultant toluene solution is analysed by gas chromatography. The yield of benzyl alcohol deriving from the reduction of the benzoyl chloride is 97%.

EXAMPLE 23

Operating by the method of example 1, 0.5 mmoles of propionic anhydride in benzene (0.5 ml of a 1 M solution) are reacted with 0.85 mmoles of $Ca[AlH_2(OisoC_4H_9)_2]_2.THF$ in benzene (2.9 ml of a 0.293 M solution) for 2.5 hours at reflux temperature. After acid hydrolysis, the resultant toluene solution is analysed by gas chromatography. The yield of n-propyl alcohol deriving from the reduction of the propionic anhydride is quantitative.

EXAMPLE 24

Operating by the method of example 1, 0.5 mmoles of pivalic anhydride in toluene (0.5 ml of a 1 M solution) are reacted with 0.6 mmoles of $Ca[AlH_2(OisoC_4H_9)_2]_2.THF$ in toluene (2.9 ml of a 0.207 M solution) for 1 hour at 80° C. After acid hydrolysis, the resultant toluene solution is analysed by gas chromatography. The yield of neopentyl alcohol deriving from the reduction of the pivalic anhydride is quantitative.

EXAMPLE 25

Operating by the method of example 1, 1 mmole of benzoyl chloride in benzene (1 ml of a 1 M solution) is reacted with 0.375 mmoles of $Ca[AlH_2(OisoC_4H_9)_2]_2.THF$ in benzene (1.95 ml of a 0.192 M solution) for 4 hours under reflux.

After acid hydrolysis, the resultant benzene solution is analysed by gas chromatography. It is found that the benzyl chloride has been converted to toluene with a yield of 55%.

EXAMPLE 26

Preparation of $Ca(AlH_2[OCH_2CH(CH_3)_2]_2)_2.THF$.

Operating under a nitrogen atmosphere, $NaAlH_4$ (50 mmoles), tetrahydrofuran (90 ml) and $CaCl_2$ (50 mmoles) are placed in a 500 ml flask provided with a filling funnel and a bulb condenser. The suspension is stirred by magnetic stirring and heated to reflux temperature. A solution of isobutyric aldehyde (100 mmoles) in tetrahydrofuran (40 ml) is added slowly to the suspension (over about 30 minutes). During the addition, the exothermic level of the reaction is sufficient to maintain the reflux temperature without the need for external heating. After the addition is completed, the mixture is allowed to cool under stirring to ambient temperature. It is then left under stirring at ambient temperature, occasionally checking the increase in the molar Ca/Al ratio in the solution, which varies as follows:

| Time - Hours (from completion of the aldehyde addition) | Molar Ca/Al ratio in solution |
|---|---|
| 4 | 0.40 |
| 7 | 0.43 |
| 9 | 0.45 |
| 12 | 0.49 |

The reaction mixture is then filtered. The solution is evaporated under reduced pressure, and the white solid residue is dried under vacuum (8 hours, ambient temperature, $10^{-2}$ mmHg) and analysed:

Found Al=12.6%; Ca=9.0%; Hatt=9.8 meq/g corresponding to Ca/Al=0.48; Hatt/Al=2.09.

Calculated for $C_{20}H_{48}Al_2CaO_5$: Al=11.7%; Ca=8.7%; Hatt=8.7 meq/g; Yield 95%.

EXAMPLE 27

Preparation of $Ca(AlH_2[OCH(CH_3)_2]_2)_2.2THF$

Operating by the method and with the quantities of example 26, $NaAlH_4$, $CaCl_2$ and acetone are reacted in THF. After the addition of acetone has been completed, the observed variations in the Ca/Al ratio in the solution are as follows:

| Time - Hours (from completion of the acetone addition) | Molar Ca/Al ratio in solution |
|---|---|
| 0 | 0.33 |
| 2 | 0.40 |
| 7 | 0.49 |

The reaction mixture is then filtered. The solution is evaporated under reduced pressure, and the white solid residue is dried under vacuum (8 hours, ambient temperature, $10^{-2}$ mmHg) and analysed:

Found Al=10.9%; Ca=7.9%; Hatt=8.1 meq/g corresponding to Ca/Al=0.49; Hatt/Al=2.01.

Calculated for $C_{20}H_{48}Al_2CaO_6$: Al=11.3%; Ca=8.4%; Hatt=8.4 meq/g; Yield 92%.

EXAMPLE 28

Preparation of $Ca(AlH_2[OCH(CH_3)_2]_2)_2.2THF$.

Operating under a nitrogen atmosphere, $NaAlH_4$ (42 mmoles), ethyl ether (90 ml) tetrahydrofuran (10 ml) and $CaCl_2$ (42 mmoles), are placed in a 500 ml flask provided with a filling funnel and a bulb condenser. The suspension is stirred by a magnetic stirrer and heated to the reflux temperature. A solution of acetone (84 mmoles) in ethyl ether (40 ml) is added slowly thereto (over about 30 minutes). During the addition, the exothermic effect of the reaction is sufficient to maintain the reflux temperature without external heating being required. After the addition is completed, stirring is continued at the reflux temperature while occasionally checking the increase in the molar Ca/Al ratio in the solution, which varies as follows

| Time - Hours (from completion of acetone addition) | Molar Ca/Al ratio in solution |
|---|---|
| 0.25 | 0.37 |
| 3.25 | 0.46 |
| 6.25 | 0.49 |

The reaction mixture is finally filtered. The solution is evaporated under reduced pressure, and the white solid residue is dried under vacuum (8 hours, ambient temperature, $10^{-2}$ mmHg) and analysed:

Found Al=10.8%; Ca=8.1%; Hatt=8.0 meq/g corresponding to Ca/Al=0.5; Hatt/Al=2.0.

Calculated for $C_{20}H_{48}Al_2CaO_6$: Al=11.3%; Ca=8.4%; Hatt=8.4 meq/g; Yield 95%.

EXAMPLE 29

Preparation of $Ca(AlH_2[OCH(CH_3)(C_2H_5)]_2)_2 \cdot THF$

Operating by the method and with the quantities of example 26, $NaAlH_4$, $CaCl_2$ and methylethylketone are reacted in tetrahydrofuran. On completion of the ketone addition, the observed variations in the Ca/Al ratio in the solution are as follows:

| Time - Hours (from completion of the ketone addition) | Molar Ca/Al ratio in solution |
|---|---|
| 0 | 0.34 |
| 2 | 0.42 |
| 7 | 0.49 |

The reaction mixture is finally filtered. The solution is evaporated under reduced pressure, and the white solid residue is dried under vacuum (8 hours, ambient temperature, $10^{-2}$ mmHg) and analysed:

Found Al=11.6%; Ca=8.5%; Hatt=8.2 meq/g corresponding to Ca/Al=0.5; Hatt/Al=1.9.

Calculated for $C_{20}H_{48}Al_2CaO_5$: Al=11.7%; Ca=8.7%; Hatt=8.7 meq/g; Yield 90%.

EXAMPLE 30

Preparation of $Ca(AlH[OCH(CH_3)(C_2H_5)]_3)_2 \cdot 2THF$

The operation is carried out as in example 29, except for the different quantity of methylethylketone (150 mmoles). On completion of the ketone addition, the solution is left under stirring at ambient temperature for 1 hour, and the molar Ca/Al ratio in the solution is measured, this being 0.49. The reaction mixture is filtered, the solution is evaporated under reduced pressure and the white solid residue is dried under vacuum (8 hours, ambient temperature, $10^{-2}$ mmHg) and analysed:

Found Al=9.5%; Ca=7.0%; Hatt=3.5 meq/g corresponding to Ca/Al=0.5; Hatt/Al=1.

Calculated for $C_{32}H_{54}Al_2CaO_8$: Al=9.3%; Ca=6.9%; Hatt=3.4 meq/g; Yield 93%.

EXAMPLE 31

Preparation of $Ca[AlH_2(OC_6H_{11})_2]_2 \cdot 2THF$

Operating by the method and with the quantities of example 26, $NaAlH_4$, $CaCl_2$ and cyclohexanone are reacted in THF. After completion of the cyclohexanone addition, the observed variations in the Ca/Al ratio in the solution are as follows:

| Time - Hours (from completion of the cyclohexanone addition) | Molar Ca/Al ratio in solution |
|---|---|
| 1 | 0.33 |
| 5 | 0.42 |
| 8 | 0.47 |
| 9 | 0.48 |

The reaction mixture is finally filtered. The solution is evaporated under reduced pressure and the solid white residue is dried under vacuum (8 hours, ambient temperature, $10^{-2}$ mmHg) and analysed:

Found Al=8.2%; Ca=5.8%; Hatt=5.8 meq/g corresponding to Ca/Al=0.48; Hatt/Al=1.92.

Calculated for $C_{32}H_{64}Al_2CaO_6$: Al=8.4%; Ca=6.3%; Hatt=6.3 meq/g; Yield 95%.

EXAMPLE 32

Preparation of $Ca[AlH_2(OC_6H_{11})_2]_2 \cdot THF$

Operating under a nitrogen atmosphere, $NaAlH_4$ (42 mmoles), toluene (90 ml), tetrahydrofuran (15 ml) and $CaCl_2$ (42 mmoles) are placed in a 500 ml flask provided with a filling funnel and a bulb condenser. The suspension is stirred by a magnetic stirrer and heated to 80° C., and a solution of cyclohexanone (84 mmoles) in toluene (35 ml) is added slowly thereto (over about 30 minutes). On completion of the addition, it is left under stirring at 80° C., while occasionally checking the increase in the molar Ca/Al ratio in the solution, which varies as follows:

| Time - Hours (from completion of the cyclohexanone addition) | Molar Ca/Al ratio in solution |
|---|---|
| 0 | 0.26 |
| 3 | 0.44 |
| 6 | 0.46 |

A further excess of $CaCl_2$ (8.5 mmoles) is added, and stirring continued at 80° C. for a further 3 hours, with the result that the molar Ca/Al ratio becomes 0.50.

The reaction mixture is filtered. The solution is evaporated under reduced pressure and the white solid residue is dried under vacuum (8 hours, ambient temperature, $10^{-2}$ mmHg) and analysed:

Found Al=10.1%; Ca=7.5%; Hatt=7.5 meq/g corresponding to Ca/Al=0.50; Hatt/Al=2.0;

Calculated for $C_{28}H_{56}Al_2CaO_5$: Al=9.5%; Ca=7.1%; Hatt=7.1 meq/g; Yield 92%.

EXAMPLE 33

Preparation of $Ca[AlH_{2.5}(OC_6H_{11})_{1.5}]_2 \cdot THF$

The operation is carried out as in example 31, except for the different quantity of cyclohexanone (75 mmoles). After completion of the ketone addition, stirring is continued for 1 hour at ambient temperature, and the molar Ca/Al ratio in the solution is measured, this being 0.49. The reaction mixture is filtered. The solution is evaporated under reduced pressure and the white solid residue is dried under vacuum (8 hours, ambient temperature, $10^{-2}$ mmHg) and analysed:

Found Al=10.9%; Ca=8.2%; Hatt=10.2 meq/g corresponding to Ca/Al=0.51; Hatt/Al=2.55.

Calculated for $C_{22}H_{46}Al_2CaO_4$: Al=11.5%; Ca=8.6%; Hatt=10.7 meq/g; Yield 97%.

We claim:

1. A process for synthesising compounds of aluminium and alkaline earth metals containing hydride hydrogens and alkoxy radicals, of composition $$M[AlH_{4-n}(OR)_n]_2 \cdot xB$$

in which $0.5 \leq n \leq 3.5$; OR is an alkoxy radical derived from a primary, secondary or tertiary alcohol; R is an aliphatic, cycloaliphatic or aromatic hydrocarbon radical; M is an alkaline earth metal; B is a Lewis base; x can vary between 0 and 4; and R can also contain functional groups OR', SR', NR'$_2$, consisting of reacting together:
(a) a halide of an alkaline earth metal;
(b) an alanate of an alkaline earth metal of formula M'AlH$_4$ (M'=alkaline metal);
(c) an alcohol chosen from primary, secondary or tertiary aliphatic, cycloaliphatic or aromatic alcohols containing 1 to 20 carbon atoms.

2. A process for synthesising mixed alkoxy hydride derivatives of aluminium and alkaline earth metals, of composition $$M[AlH_{4-n}(OR)_n]_2 \cdot xB \qquad (I)$$

in which $0.5 \leq n \leq 3.5$; OR is an alkoxy radical derived from a primary or secondary alcohol; R is an aliphatic, cycloaliphatic or aromatic hydrocarbon radical; M is an alkaline earth metal; B is a Lewis base; and x can vary between 0 and 4, consisting of reacting an alanate of an alkaline metal and a halide of an alkaline earth metal with an aldehyde or ketone.

3. A process as claimed in claim 1, wherein the reaction is conducted in an ether organic solvent or in an aliphatic or aromatic hydrocarbon.

4. A process as claimed in claim 1, wherein the solvent is chosen from diethylether, methyl-tert-butyl ether, tetrahydrofuran, benzene, toluene, hexane and heptane.

5. A process as claimed in claim 1, wherein the reaction is conducted at a temperature between $-40°$ C. and the product decomposition temperature.

6. A process as claimed in claim 1, wherein the alcohol used is chosen from alcohols containing functional groups in a chain.

7. A process as claimed in claim 1, wherein the alcohol contains amine, ether or phosphine functions in a chain.

* * * * *